Figure 1:
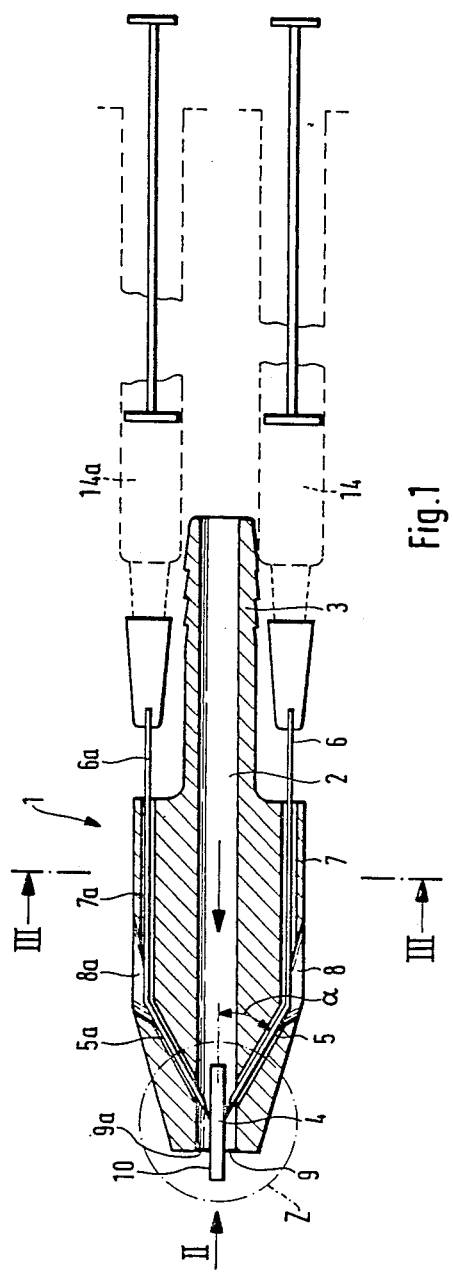

United States Patent [19]

Zimmermann

[11] Patent Number: 4,846,405

[45] Date of Patent: Jul. 11, 1989

[54] SPRAY HEAD FOR THE ADMINISTRATION OF A MULTI-COMPONENT MATERIAL BY MEANS OF GAS

[75] Inventor: Josef Zimmermann, Sulzbach, Fed. Rep. of Germany

[73] Assignee: Hoechst Aktiengesellschaft, Frankfurt am Main, Fed. Rep. of Germany

[21] Appl. No.: 226,309

[22] Filed: Jul. 29, 1988

[30] Foreign Application Priority Data

Aug. 1, 1987 [DE] Fed. Rep. of Germany ....... 3725552

[51] Int. Cl.$^4$ .................. F23D 11/16; B05B 1/14; B05B 7/06; A61M 37/00
[52] U.S. Cl. .................. 239/422; 239/424.5; 239/429; 239/432; 239/552; 604/83
[58] Field of Search ........... 239/552, 418, 422, 424.5, 239/290, 429, 432, 433; 222/135, 630, 637; 604/83, 56, 191

[56] References Cited

U.S. PATENT DOCUMENTS 2,321,792  6/1943  Bowie ................... 239/77
2,901,112  8/1959  Naftulin et al. ........... 604/83
3,623,669 11/1971  Woods ................... 239/422
3,650,474  3/1972  Riebling ................. 239/418
4,631,055 12/1986  Redl et al. ............... 604/191

FOREIGN PATENT DOCUMENTS 737249  6/1966  Canada ................... 604/83
037393  4/1981  European Pat. Off. .

Primary Examiner—Andres Kashnikow
Assistant Examiner—Patrick N. Burkhart
Attorney, Agent, or Firm—Finnegan, Henderson, Farabow, Garrett and Dunner

[57] ABSTRACT

In the spray head for the administration of a multi-component material by means of gas, a gas channel (2) with gas connection (3) is provided, which channel is divided by a separating web (4) into a plurality of channels (2a, 2b) running parallel to the separating web. Into these channels there open out boreholes (5, 5a) for receiving cannulas. The open ends of the boreholes (5, 5a) go into grooves (7, 7a) which serve for guiding the cannulas (6, 6a). The grooves are arranged parallel to the gas channel (2). The separating web (4) protrudes beyond the channel ends (9, 9a).

1 Claim, 3 Drawing Sheets

SPRAY HEAD FOR THE ADMINISTRATION OF A MULTI-COMPONENT MATERIAL BY MEANS OF GAS

DESCRIPTION

The invention relates to a spray head for the administration of a multi-component material, in particular for the administration of surgical histoadhesive.

An apparatus for the administration of surgical histoadhesive is known from European Patent Specification No. 0,037,393. The syringe elements for the components fibrinogen solution and thrombin solution are connected via cones to delivery channels of a spray head. The spray head has a feed channel for gas, which divides inside the spray head into two branches, the outlet openings of which are arranged in the region of the mouths of the delivery channels and are disposed at an angle to each other and are directed at right angles to the outlet opening of the components. The components, which are fed via the syringe elements (reciprocating pumps), are sprayed by the gas. The spray cones join, depending on the size of the angle which the spray axes form, at a greater or lesser distance away from the mouths of the delivery channels, where they mix together and the components react with each other. It is disadvantageous that accurate spraying is not possible with this spray head, as the object to be sprayed must lie precisely at the intersection of the spray jets if a satisfactory result is to be achieved.

The invention is to provide a remedy here. According to the invention, as it is defined in the claim, the object is achieved by a spray head which has a gas channel with gas connection, which is divided by a separating web into a plurality of channels running parallel to the separating web, into these channels there open boreholes for receiving cannulas, the open ends of which go into grooves for guiding the cannulas which are arranged parallel to the gas channel in the spray head and the separating web protrudes beyond the channel ends. The boreholes for the cannulas may open out at an angle $\alpha \leq 90°$ into the channels running parallel to the separating web.

The advantages achieved with the invention are to be seen in particular in that the coalescence of the components directly behind the end of the separating web produces a slender spray cone, which makes possible a uniform mixing of the components and an accurate spraying of the objects even from close to at low spraying pressure. The separating web also has the effect of avoiding premature contact of the different components with one another, which would lead to blockages of the channels. The spray head is suitable in particular for administration of surgical histoadhesive, which is formed from the components in situ after passing the separating web end.

Figure 2:
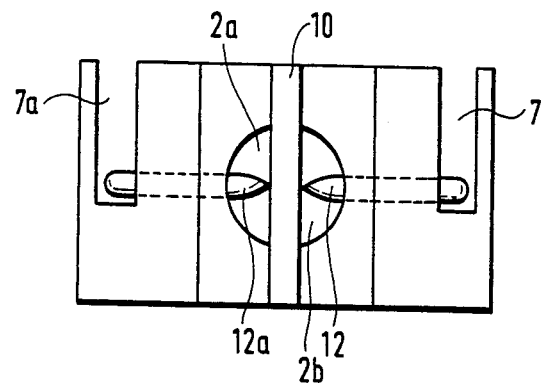
Figure 3:
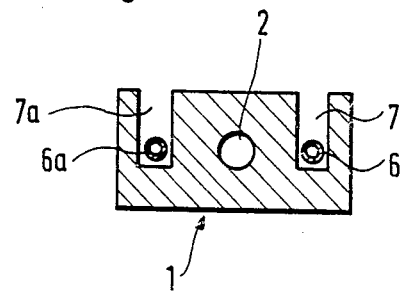
Figure 4:
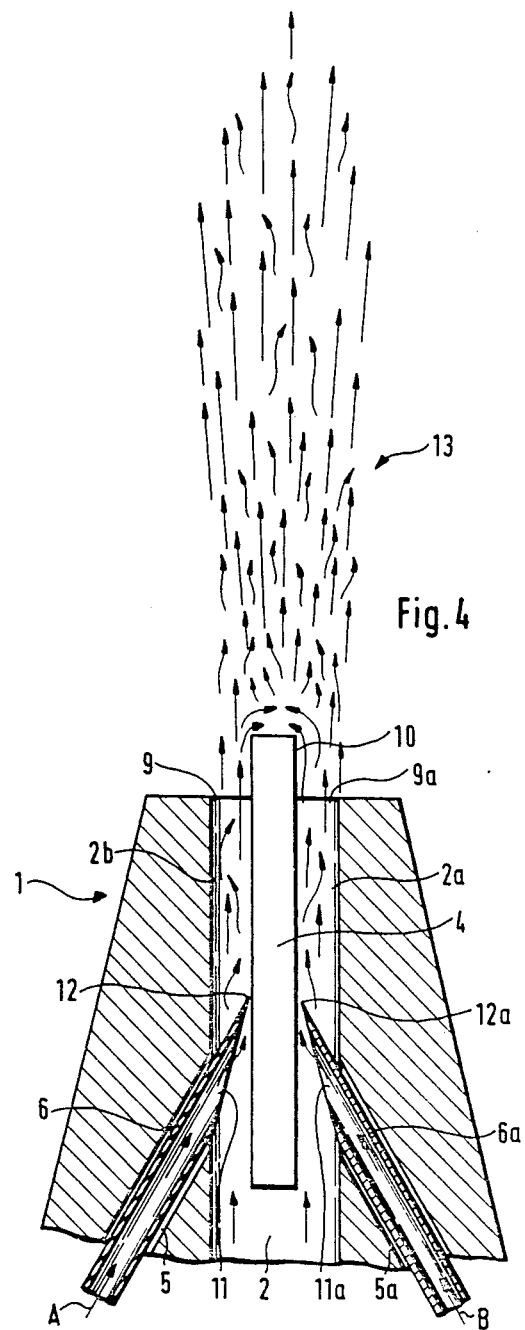

The invention is explained in more detail below by drawings showing merely one embodiment and in which:

FIG. 1 shows the spray head in sectional plan view,
FIG. 2 shows the view II of FIG. 1,
FIG. 3 shows the section III—III of FIG. 1 and
FIG. 4 shows the cutaway "Z" of FIG. 1 with spray pattern in plan view.

The spray head 1 has a gas channel 2 with gas connection 3. In the gas channel 2 there is arranged a separating web 4, which divides the gas channel into a plurality of channels 2a, 2b running parallel to the separating web. Into the channels 2a, 2b there open out boreholes 5, 5a for receiving cannulas 6, 6a. For guiding the cannulas in the spray head, the open ends of the boreholes 5, 5a go into grooves 7, 7a which are arranged parallel to the gas channel 2 in the spray head 1. In order to prevent a premature mixing of the components, the web 4 protrudes beyond the channel ends 9, 9a. The recesses 8, 8a serve for the insertion of the cannulas into the boreholes. After insertion, the cannulas are hooked into the grooves 7, 7a and fixed in place. The tips 12, 12a of the cannulas are to butt against the separating web 4 and their sloped openings 11, 11a are to be directed against the flow direction of the gas. The end 10 of the separating web protruding from the spray head 1 may be made angular or rounded-off. The components A and B are fed via the cannulas 6, 6a to the gas channels 2a, 2b, entrained by the gas (air) and swirled behind the end 10 of the separating web 4, so that they can react. 13 indicates the spray pattern and 14, 14a indicate the disposable syringes for the components A and B. If the multi-component material consists of three or more components, the separating web 4 may be designed triangularly or polygonally in cross-section, so that the gas channel 2 is divided according to the number of components. Then the same number of boreholes with recesses and grooves open out into these channels.

I claim:

1. A spray head for the administration of a multicomponent material by means of gas, wherein the spray head (1) has a gas channel (2) with gas connection (3), which is divided by a separating web (4) into a plurality of channels (2a, 2b) running parallel to the separating web (4), into these channels (2a, 2b) there open out boreholes (5, 5a) for receiving cannulas (6, 6a), the open ends of the boreholes (5, 5a) go into grooves (7, 7a) for guiding the cannulas (6, 6a) which are arranged parallel to the gas channel (2) in the spray head (1), and the separating web (4) protrudes beyond the channel ends (9, 9a).

* * * * *